(12) United States Patent
Eliason et al.

(10) Patent No.: US 9,318,649 B2
(45) Date of Patent: Apr. 19, 2016

(54) MULTI-WAVELENGTH LED CURING LAMP

(71) Applicant: Phoseon Technology, Inc., Hillsboro, OR (US)

(72) Inventors: Garth Eliason, Portland, OR (US); Doug Childers, Portland, OR (US)

(73) Assignee: Phoseon Technology, Inc., Hillsboro, OR (US)

( * ) Notice: Subject to any disclaimer, the term of this patent is extended or adjusted under 35 U.S.C. 154(b) by 141 days.

(21) Appl. No.: 14/037,115

(22) Filed: Sep. 25, 2013

(65) Prior Publication Data

US 2015/0083933 A1    Mar. 26, 2015

(51) Int. Cl.
   *G01N 21/64* (2006.01)
   *H01L 33/06* (2010.01)
   *B29C 35/08* (2006.01)

(52) U.S. Cl.
   CPC ............ *H01L 33/06* (2013.01); *B29C 35/0805* (2013.01); *B29C 2035/0827* (2013.01); *G01N 21/64* (2013.01)

(58) Field of Classification Search
   CPC ..................................................... G01N 21/64
   See application file for complete search history.

(56) References Cited

U.S. PATENT DOCUMENTS

| | | | |
|---|---|---|---|
| 6,560,038 B1 * | 5/2003 | Parkyn et al. | 359/726 |
| 6,661,029 B1 * | 12/2003 | Duggal | 257/89 |
| 7,750,359 B2 * | 7/2010 | Narendran et al. | 257/98 |
| 8,120,239 B2 * | 2/2012 | Cheon | G02F 2/02 313/486 |
| 2006/0066210 A1 * | 3/2006 | Ng et al. | 313/486 |
| 2006/0145599 A1 * | 7/2006 | Stegamat et al. | 313/504 |
| 2007/0053184 A1 * | 3/2007 | Brukilacchio | 362/231 |
| 2007/0165404 A1 * | 7/2007 | Cheng | 362/253 |
| 2008/0117500 A1 * | 5/2008 | Narendran | H01L 33/507 359/326 |
| 2008/0173886 A1 * | 7/2008 | Cheon | C09K 11/02 257/98 |
| 2010/0123155 A1 * | 5/2010 | Pickett | B82Y 15/00 257/98 |
| 2011/0119949 A1 * | 5/2011 | Kites | B05D 3/061 34/275 |
| 2013/0070443 A1 * | 3/2013 | Pan et al. | 362/84 |
| 2013/0112942 A1 | 5/2013 | Kurtin et al. | |

(Continued)

FOREIGN PATENT DOCUMENTS

| | | |
|---|---|---|
| KR | 20080080199 A | 9/2008 |
| KR | 20100053409 A | 5/2010 |
| KR | 20130061382 A | 6/2013 |
| WO | 2013055772 A1 | 4/2013 |

OTHER PUBLICATIONS

Kim, Kyungnam et al. "Photoenhancement of a Quantum Dot Nanocomposite via UV Annealing and its Application to White LEDs", Advanced Materials, vol. 23, No. 7, Dec. 27, 2010, pp. 911-914.

(Continued)

*Primary Examiner* — Christine Sung
(74) *Attorney, Agent, or Firm* — Alleman Hall McCoy Russell & Tuttle LLP

(57) ABSTRACT

A curing device may comprise a first array of LED's, each LED of the first array emitting radiation substantially centered at a first excitation wavelength onto a quantum dot layer, the quantum dot layer positioned above the first array of LED's and configured to partially absorb the first excitation wavelength radiation and down convert the absorbed first excitation wavelength radiation, and partially transmit the emitted first excitation wavelength radiation, wherein the down converted and the partially transmitted first excitation wavelength radiation are directed onto a radiation-curable workpiece.

13 Claims, 6 Drawing Sheets

(56) References Cited

U.S. PATENT DOCUMENTS

| | | | | |
|---|---|---|---|---|
| 2013/0277643 A1* | 10/2013 | Williamson et al. | ............ | 257/13 |
| 2014/0158982 A1* | 6/2014 | Park et al. | ................. | 257/13 |
| 2014/0246689 A1* | 9/2014 | Luo et al. | ................. | 257/98 |
| 2014/0254131 A1* | 9/2014 | Osinski | ............ | F21K 9/56 362/84 |
| 2015/0048395 A1* | 2/2015 | Vampola et al. | ............ | 257/89 |

OTHER PUBLICATIONS

ISA Korean Intellectual Property Office, International Search Report and Written Opinion of PCT/US2014/054563, Dec. 22, 2014, 9 pages.

* cited by examiner

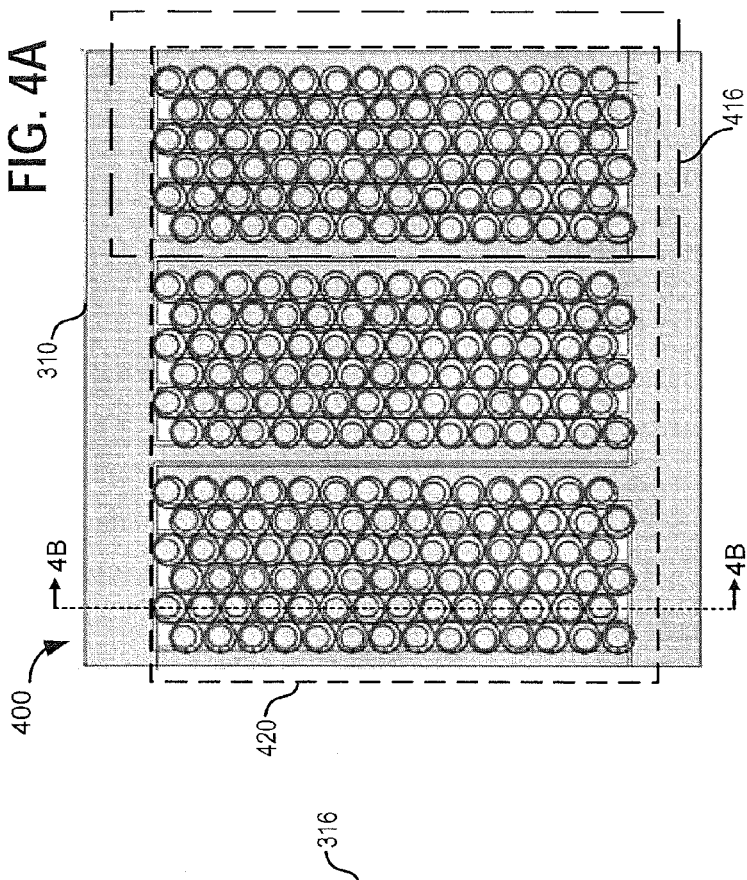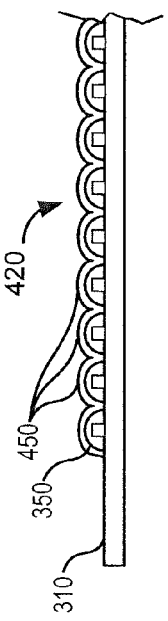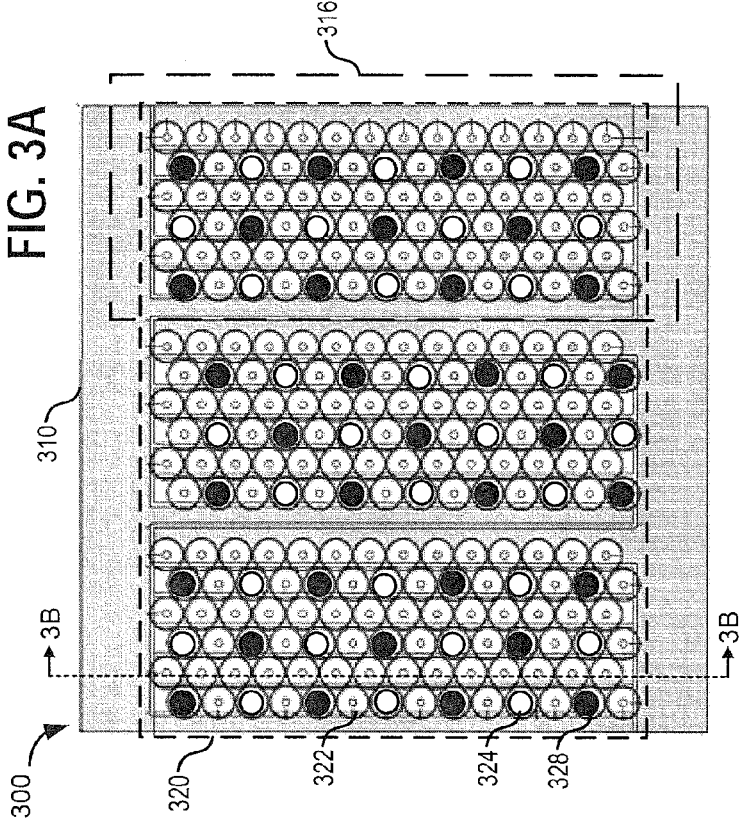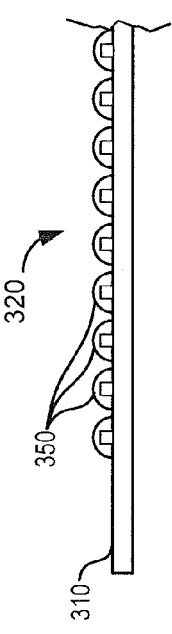

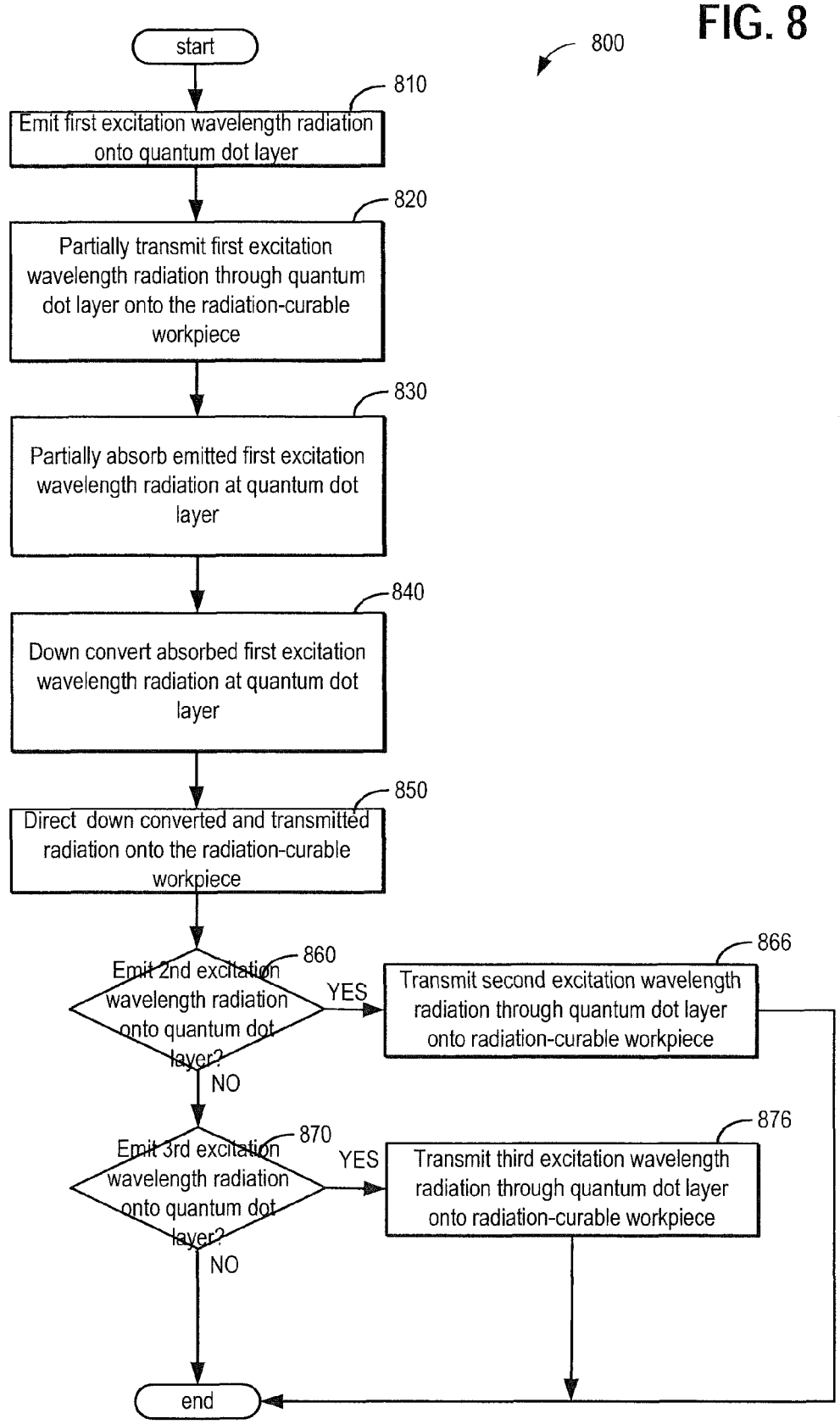

MULTI-WAVELENGTH LED CURING LAMP

BACKGROUND AND SUMMARY

Conventional lamp curing technology based on gas discharge lamps, such as mercury arc lamps, emit broad spectrum UV radiation generally from 300 nm (mid-UV range) to approximately 570 nm, with several characteristic emission lines making up the spectral content. Gas discharge lamps require high voltages to operate, have short lifetimes of approximately 15,000 hours, and require active cooling to maintain stable operation, making the costs of operation high.

With the advent of gallium nitride (GaN) based LEDs, the ability to create solid-state, semiconductor semiconductor light sources with high enough UV energies, (shorter wavelengths), has given rise to LED-based curing lamps. GaN LED technology enables curing lamps that are more compact with lower input power requirements, lower operating costs, and longer lifetimes. While LED-based curing lamps offer clear advantages over gas discharge lamps, they are typically limited to a single wavelength (e.g. 395 nm or 365 nm for UVA curing applications). As such, most UV-cured materials may require adjustments in formulation to cure efficiently at 395 nm or other singular wavelengths. However, there remain applications and systems that require a broader spectral content for efficient and complete curing, such as the emission spectra afforded through the use of conventional mercury arc lamps.

Kurtin et al. disclose a lighting apparatus including an LED emitting blue or UV light and a plurality of quantum dots. The quantum dots may be applied proximal to the LED and provide down-conversion or upshifting of blue or UV light emitted from the LED to emit red, green, yellow, orange, blue, indigo, violet or other visible light having a wavelength from 380-780 nm. Kurtin further discloses that the absorption and emission spectrum of each quantum dot are essentially non-overlapping.

The inventors herein have recognized potential issues with the above approach. Namely, Kurtin is directed to providing a lighting apparatus for emitting visible light. In particular, Kurtin is directed to absorbing and down converting blue and UV light to visible light via quantum dots, and emitting the visible light therefrom. As such, Kurtin's lighting apparatus does not address the problem of providing broad emission spectra for UV curing such as that of conventional mercury arc lamps. Furthermore, Kurtin's lighting apparatus does not emit UV radiation below 380 nm. Accordingly, Kurtin's lighting apparatus is not suited for applications requiring a broad UV spectral content for efficient curing.

One approach that addresses the aforementioned issues includes a curing device, comprising a first array of LED's, each LED of the first array emitting radiation substantially centered at a first excitation wavelength onto a quantum dot layer, the quantum dot layer positioned above the first array of LED's and configured to partially absorb the first excitation wavelength radiation and down convert the absorbed first excitation wavelength radiation, and partially transmit the emitted first excitation wavelength radiation, wherein the down converted and the partially transmitted first excitation wavelength radiation are directed onto a radiation-curable workpiece.

In another embodiment, a method of curing a workpiece, comprises emitting radiation substantially centered at a first excitation wavelength from an array of LED's onto a quantum dot layer, only partially transmitting the first excitation wavelength radiation through the quantum dot layer onto a radiation-curable workpiece, only partially absorbing the emitted first excitation wavelength radiation at the quantum dot layer, and responsive to absorbing the excitation wavelength radiation, down converting the absorbed first excitation wavelength radiation at the quantum dot layer and emitting the down converted radiation onto the radiation-curable workpiece.

In a further embodiment a method, comprises emitting UV radiation onto a quantum dot layer, only partially absorbing and down converting the UV radiation substantially centered at 365 nm at the quantum dot layer, and only partially transmitting the UV radiation substantially centered at 365 nm through the quantum dot layer.

It will be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

FIG. 3A illustrates a plan view of an LED array.

FIG. 3B illustrates a cross-section of the LED array of FIG. 3A.

FIG. 4A illustrates a plan view of an LED array.

FIG. 4B illustrates a cross-section of the LED array of FIG. 4A.

FIG. 8 illustrates a flowchart of an example method of curing a workpiece.

DETAILED DESCRIPTION

Figure 1:
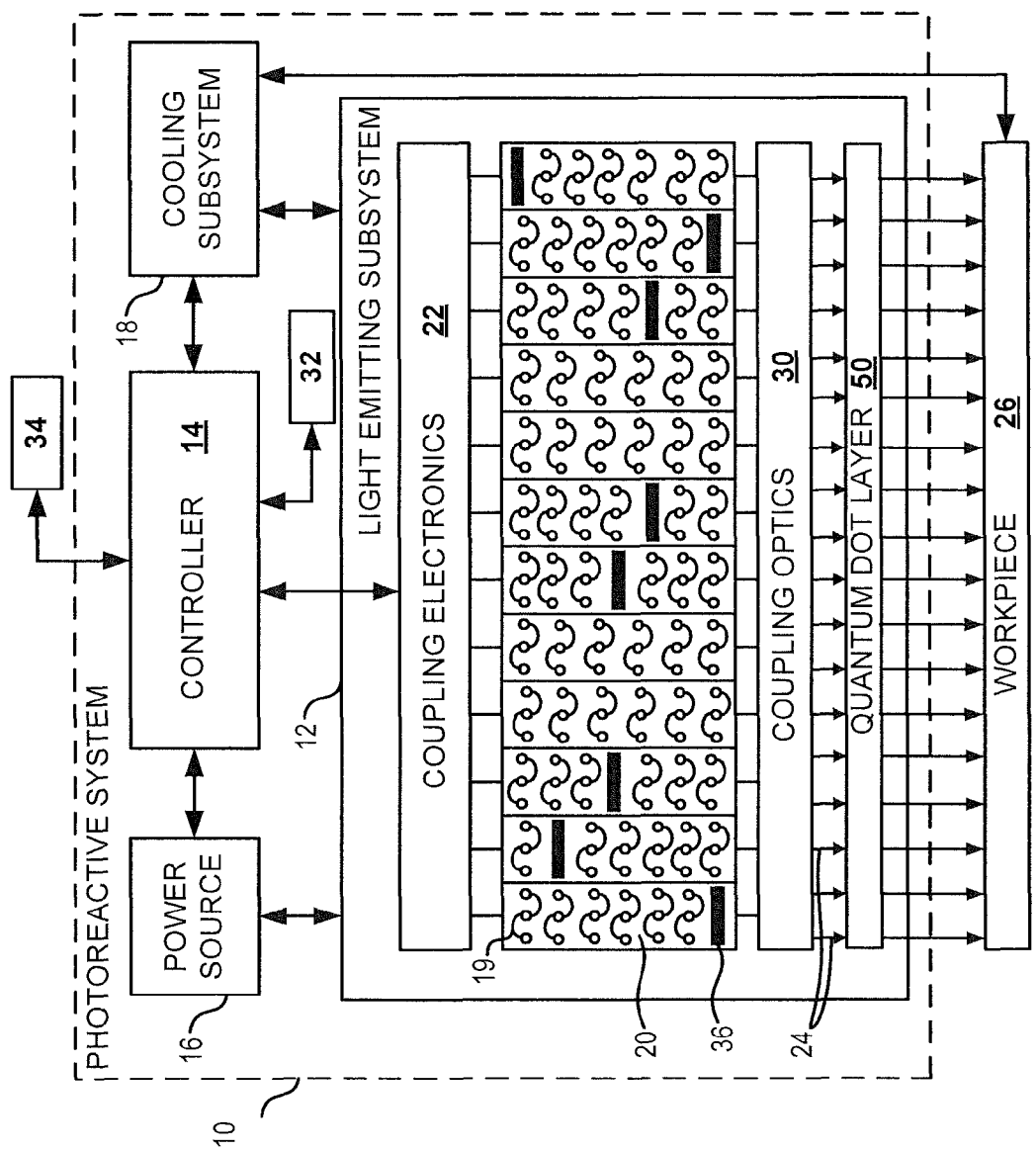
FIG. 1 illustrates a schematic of an example of a photoreactive system.
Figure 2:
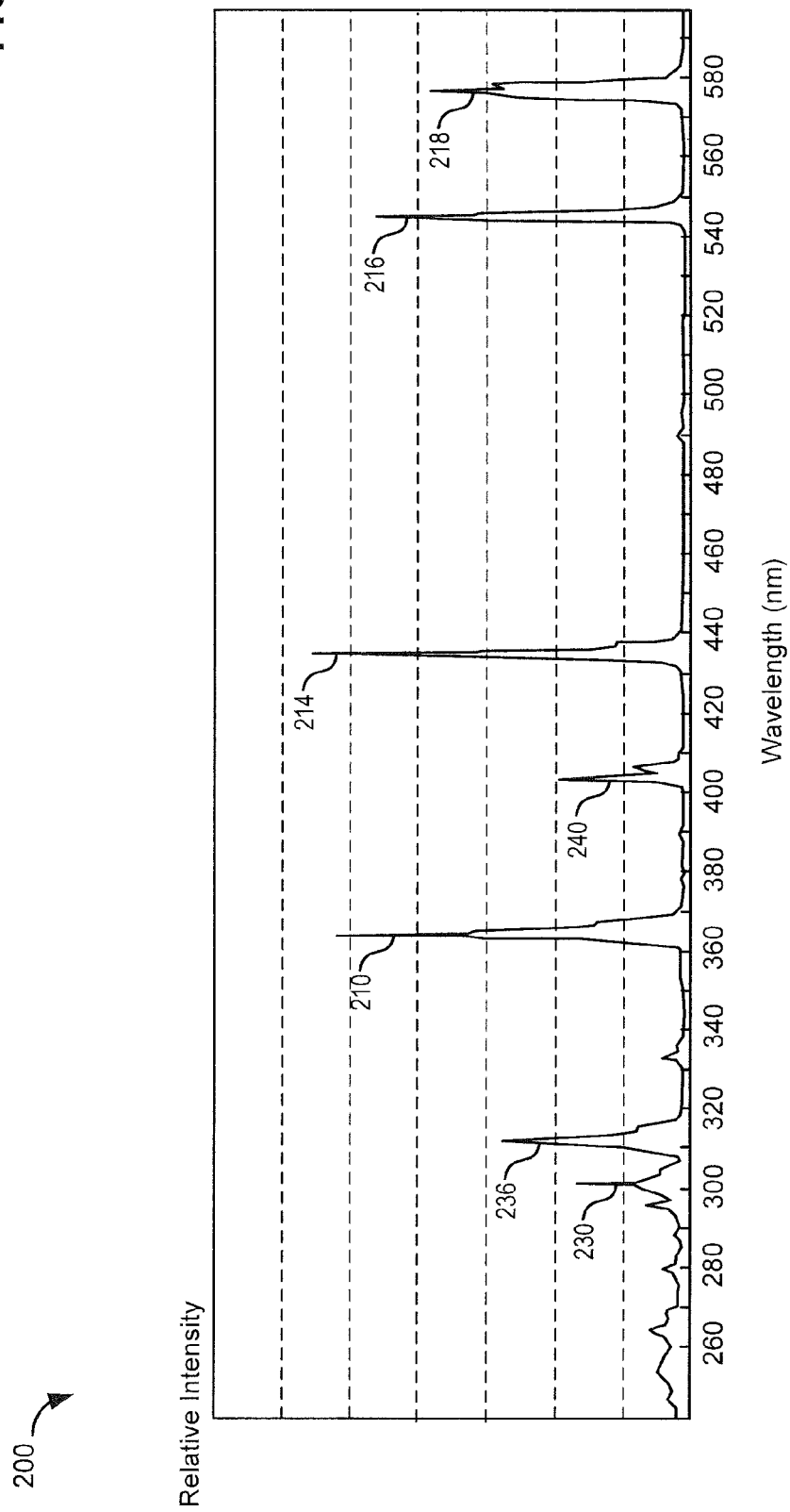
FIG. 2 illustrates an example of an emission spectrum from a curing device or a photoreactive system.
Figure 5:
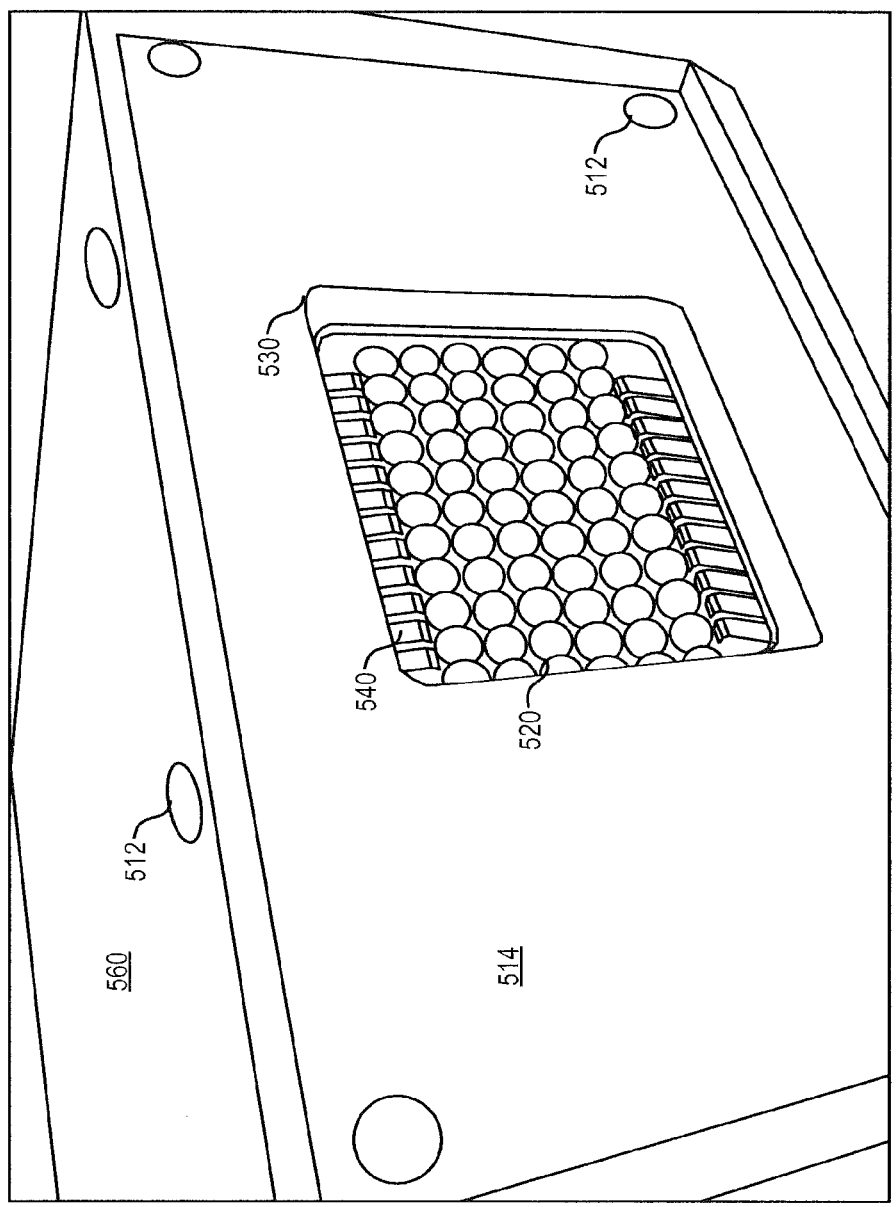
FIG. 5 illustrates an example of a curing device.

The present description is for a curing device, method and photoreactive system for curing workpieces. FIGS. 1 and 5 illustrate an example of a photoreactive system and a UV curing device, respectively, comprising an array of light-emitting elements and a quantum dot layer. FIG. 2 shows an example emission spectrum of a conventional gas discharge lamp, such as a mercury vapor lamp. FIGS. 3A, 3B, 4A, and 4B illustrate example configurations of LED arrays with and without a quantum dot layer applied to the LED array. FIGS. 6A, 6B, 7A, and 7B illustrate example configurations of UV curing devices comprising the LED arrays shown in FIGS. 3A, 3B, 4A, and 4B. FIG. 8 illustrates a flowchart showing an example method for curing a workpiece.

Referring now to FIG. 1, it illustrates a block diagram for an example configuration of a photoreactive system such as curing device 10. In one example, curing device 10 may comprise a light-emitting subsystem 12, a controller 14, a power source 16 and a cooling subsystem 18. The light-emitting subsystem 12 may comprise a plurality of semiconductor devices 19. The plurality of semiconductor devices 19 may be an array 20 of light-emitting elements such as a linear array of LED devices, for example. Array 20 of light-emitting elements may also comprise a two-dimensional array of LED devices, or an array of LED arrays, for example. Semiconductor devices may provide radiant output 24. The radiant output 24 may be directed to a workpiece 26 located at a fixed plane from curing device 10. Returned radiation 28 may be directed back to the light-emitting subsystem 12 from the workpiece 26 (e.g., via reflection of the radiant output 24).

The radiant output 24 may be directed to the workpiece 26 via coupling optics 30. The coupling optics 30, if used, may be variously implemented. As an example, the coupling optics may include one or more layers, materials or other structures interposed between the semiconductor devices 19. As an example, the coupling optics 30 may include a micro-lens array to enhance collection, condensing, collimation or otherwise the quality or effective quantity of the radiant output 24. In one example, the micro-lenses may be index-matched to the LED chips to increase transmission of light emitted from the micro-lens array. As another example, the coupling optics 30 may include a micro-reflector array. In employing such a micro-reflector array, each semiconductor device providing radiant output 24 may be disposed in a respective micro-reflector, on a one-to-one basis. As another example, an array of semiconductor devices 20 providing radiant output 24 may be disposed in macro-reflectors, on a many-to-one basis. In this manner, coupling optics 30 may include both micro-reflector arrays, wherein each semiconductor device is disposed on a one-to-one basis in a respective micro-reflector, and macro-reflectors wherein the quantity and/or quality of the radiant output 24 from the semiconductor devices is further enhanced by macro-reflectors. For example, macro-reflectors may comprise elliptic cylindrical reflectors, parabolic reflectors, dual elliptic cylindrical reflectors, and the like.

Each of the layers, materials or other structure of coupling optics 30 may have a selected index of refraction. By properly selecting each index of refraction, reflection at interfaces between layers, materials and other structures in the path of the radiant output 24 (and/or returned radiation 28) may be selectively controlled. As an example, by controlling differences in such indexes of refraction at a selected interface, for example window 64, disposed between the semiconductor devices to the workpiece 26, reflection at that interface may be reduced or increased so as to enhance the transmission of radiant output at that interface for ultimate delivery to the workpiece 26. For example, the coupling optics may include a dichroic reflector where certain wavelengths of incident light are absorbed, while others are reflected and focused to the surface of workpiece 26.

The coupling optics 30 may be employed for various purposes. Example purposes include, among others, to protect the semiconductor devices 19, to retain cooling fluid associated with the cooling subsystem 18, to collect, condense and/or collimate the radiant output 24, to collect, direct or reject returned radiation 28, or for other purposes, alone or in combination. As a further example, the curing device 10 may employ coupling optics 30 so as to enhance the effective quality, uniformity, or quantity of the radiant output 24, particularly as delivered to the workpiece 26.

Curing device 10 may further comprise a quantum dot layer 50 interposed between the array 20 of light-emitting elements and the workpiece 26, and positioned above the array 20 of light-emitting elements. Quantum dot layer 50 may be applied directly to the array 20 of light-emitting elements or may be applied to a surface of a window 730 positioned over, and facing the array 20 of light-emitting elements.

Quantum dots may also be referred to as semiconductor nanocrystals, fluorescent nanoparticles and possibly others. When quantum dots are illuminated with a primary energy source, a secondary emission of energy occurs at a frequency that corresponds to the bandgap of the semiconductor material used in the quantum dot. In quantum confined particles, the bandgap energy is a function of the size and/or composition of the nanocrystal. A mixed population of quantum dots of various sizes and/or compositions can be excited simultaneously using a substantially single wavelength of light and the detectable luminescence can be engineered to occur at a plurality of wavelengths. The luminescent emission is related to the size and/or the composition of the constituent quantum dots of the population. Furthermore, quantum dots can be made highly luminescent through the use of a shell material which efficiently encapsulates the surface of the quantum dot core. In some examples, a "core/shell" quantum dot has a high quantum efficiency and significantly increased photochemical stability. The surface of the core/shell quantum dot can be modified to produce quantum dots that can be coupled to a variety of substrates.

Quantum dots are a class of fluorescent nanoparticles that absorb light in the ultraviolet (UV) or violet region and emit in the visible to near-infrared (NIR) region. Quantum dots have a relatively broad absorption curve (several hundreds of nanometers), but very narrow emission curves. The absorption curve may be nonlinear and may exhibit an exponentially-increasing curvature with shorter excitation wavelengths. The light intensity emitted by quantum dots may be proportional to the absorbed light intensity, so as either the intensity of the excitation is increased or its wavelength is decreased, the quantum dot emission may become brighter. Regardless of the intensity of the excitation light or its wavelength, the emission band shape of a particular quantum dot species remains constant. Quantum dots are available in a range of emission wavelengths.

Selected of the plurality of semiconductor devices 19 may be coupled to the controller 14 via coupling electronics 22, so as to provide data to the controller 14. As described further below, the controller 14 may also be implemented to control such data-providing semiconductor devices, e.g., via the coupling electronics 22. The controller 14 may be connected to, and may be implemented to control, the power source 16, and the cooling subsystem 18. For example, the controller may supply a larger drive current to light-emitting elements distributed in the middle portion of array 20 and a smaller drive current to light-emitting elements distributed in the end portions of array 20 in order to increase the useable area of light irradiated at workpiece 26. Moreover, the controller 14 may receive data from power source 16 and cooling subsystem 18. In one example, the irradiance at one or more locations at the workpiece 26 surface may be detected by sensors and transmitted to controller 14 in a feedback control scheme. In a further example, controller 14 may communicate with a controller of another lighting system (not shown in FIG. 1) to coordinate control of both lighting systems. For example, controllers 14 of multiple lighting systems may operate in a master-slave cascading control algorithm, where the setpoint of one of the controllers is set by the output of the other controller. Other control strategies for operation of curing device 10 in conjunction with another lighting system may also be used. As another example, controllers 14 for multiple lighting systems arranged side by side may control lighting systems in an identical manner for increasing uniformity of irradiated light across multiple lighting systems.

In addition to the power source 16, cooling subsystem 18, and light-emitting subsystem 12, the controller 14 may also be connected to, and implemented to control internal element 32, and external element 34. Internal element 32, as shown, may be internal to the curing device 10, while external element 34, as shown, may be external to the curing device 10, but may be associated with the workpiece 26 (e.g., handling, cooling or other external equipment) or may be otherwise related to a photoreaction (e.g. curing) that curing device 10 supports.

The data received by the controller 14 from one or more of the power source 16, the cooling subsystem 18, the light-emitting subsystem 12, and/or elements 32 and 34, may be of various types. As an example the data may be representative of one or more characteristics associated with coupled semiconductor devices 19. As another example, the data may be representative of one or more characteristics associated with the respective light-emitting subsystem 12, power source 16, cooling subsystem 18, internal element 32, and external element 34 providing the data. As still another example, the data may be representative of one or more characteristics associated with the workpiece 26 (e.g., representative of the radiant output energy or spectral component(s) directed to the workpiece). Moreover, the data may be representative of some combination of these characteristics.

The controller 14, in receipt of any such data, may be implemented to respond to that data. For example, responsive to such data from any such component, the controller 14 may be implemented to control one or more of the power source 16, cooling subsystem 18, light-emitting subsystem 12 (including one or more such coupled semiconductor devices), and/or the elements 32 and 34. As an example, responsive to data from the light-emitting subsystem indicating that the light energy is insufficient at one or more points associated with the workpiece, the controller 14 may be implemented to either (a) increase the power source's supply of power to one or more of the semiconductor devices, (b) increase cooling of the light-emitting subsystem via the cooling subsystem 18 (e.g., certain light-emitting devices, if cooled, provide greater radiant output), (c) increase the time during which the power is supplied to such devices, or (d) a combination of the above.

Individual semiconductor devices 19 (e.g., LED devices) of the light-emitting subsystem 12 may be controlled independently by controller 14. For example, controller 14 may control a first group of one or more individual LED devices to emit light of a first intensity, wavelength, and the like, while controlling a second group of one or more individual LED devices to emit light of a different intensity, wavelength, and the like. The first group of one or more individual LED devices may be within the same array 20 of semiconductor devices, or may be from more than one array of semiconductor devices 20 from multiple curing devices 10. Array 20 of semiconductor device may also be controlled independently by controller 14 from other arrays of semiconductor devices in other lighting systems. For example, the semiconductor devices of a first array may be controlled to emit light of a first intensity, wavelength, and the like, while those of a second array in another curing device may be controlled to emit light of a second intensity, wavelength, and the like.

As a further example, under a first set of conditions (e.g. for a specific workpiece, photoreaction, and/or set of operating conditions) controller 14 may operate curing device 10 to implement a first control strategy, whereas under a second set of conditions (e.g. for a specific workpiece, photoreaction, and/or set of operating conditions) controller 14 may operate curing device 10 to implement a second control strategy. As described above, the first control strategy may include operating a first group of one or more individual semiconductor devices (e.g., LED devices) to emit light of a first intensity, wavelength, and the like, while the second control strategy may include operating a second group of one or more individual LED devices to emit light of a second intensity, wavelength, and the like. The first group of LED devices may be the same group of LED devices as the second group, and may span one or more arrays of LED devices, or may be a different group of LED devices from the second group, but the different group of LED devices may include a subset of one or more LED devices from the second group.

The cooling subsystem 18 may be implemented to manage the thermal behavior of the light-emitting subsystem 12. For example, the cooling subsystem 18 may provide for cooling of light-emitting subsystem 12, and more specifically, the semiconductor devices 19. The cooling subsystem 18 may also be implemented to cool the workpiece 26 and/or the space between the workpiece 26 and the curing device 10 (e.g., the light-emitting subsystem 12). For example, cooling subsystem 18 may comprise an air or other fluid (e.g., water) cooling system. Cooling subsystem 18 may also include cooling elements such as cooling fins attached to the semiconductor devices 19, or array 20 thereof, or to the coupling optics 30. For example, cooling subsystem may include blowing cooling air over the coupling optics 30, wherein the coupling optics 30 are equipped with external fins to enhance heat transfer.

The curing device 10 may be used for various applications. Examples include, without limitation, curing applications ranging from ink printing to the fabrication of DVDs and lithography. The applications in which the curing device 10 may be employed can have associated operating parameters. That is, an application may have associated operating parameters as follows: provision of one or more levels of radiant power, at one or more wavelengths, applied over one or more periods of time. In order to properly accomplish the photoreaction associated with the application, optical power may be delivered at or near the workpiece 26 at or above one or more predetermined levels of one or a plurality of these parameters (and/or for a certain time, times or range of times).

In order to follow an intended application's parameters, the semiconductor devices 19 providing radiant output 24 may be operated in accordance with various characteristics associated with the application's parameters, e.g., temperature, spectral distribution and radiant power. At the same time, the semiconductor devices 19 may have certain operating specifications, which may be associated with the semiconductor devices' fabrication and, among other things, may be followed in order to preclude destruction and/or forestall degradation of the devices. Other components of the curing device 10 may also have associated operating specifications. These specifications may include ranges (e.g., maximum and minimum) for operating temperatures and applied electrical power, among other parameter specifications.

Accordingly, the curing device 10 may support monitoring of the application's parameters. In addition, the curing device 10 may provide for monitoring of semiconductor devices 19, including their respective characteristics and specifications. Moreover, the curing device 10 may also provide for monitoring of selected other components of the curing device 10, including its characteristics and specifications.

Providing such monitoring may enable verification of the system's proper operation so that operation of curing device 10 may be reliably evaluated. For example, curing device 10 may be operating improperly with respect to one or more of the application's parameters (e.g. temperature, spectral distribution, radiant power, and the like), any component's characteristics associated with such parameters and/or any component's respective operating specifications. The provision of monitoring may be responsive and carried out in accordance with the data received by the controller 14 from one or more of the system's components.

Monitoring may also support control of the system's operation. For example, a control strategy may be implemented via the controller 14, the controller 14 receiving and being responsive to data from one or more system components. This control strategy, as described above, may be implemented directly (e.g., by controlling a component through control signals directed to the component, based on data respecting that components operation) or indirectly (e.g., by controlling a component's operation through control signals directed to adjust operation of other components). As an example, a semiconductor device's radiant output may be adjusted indirectly through control signals directed to the power source 16 that adjust power applied to the light-emitting subsystem 12 and/or through control signals directed to the cooling subsystem 18 that adjust cooling applied to the light-emitting subsystem 12.

Control strategies may be employed to enable and/or enhance the system's proper operation and/or performance of the application. In a more specific example, control may also be employed to enable and/or enhance balance between the array's radiant output and its operating temperature, so as, e.g., to preclude heating the semiconductor devices 19 beyond their specifications while also directing sufficient radiant energy to the workpiece 26, for example, to carry out a photoreaction of the application.

In some applications, high radiant power may be delivered to the workpiece 26. Accordingly, the light-emitting subsystem 12 may be implemented using an array of light-emitting semiconductor devices 20. For example, the light-emitting subsystem 12 may be implemented using a high-density, light-emitting diode (LED) array. Although LED arrays may be used and are described in detail herein, it is understood that the semiconductor devices 19, and arrays 20 thereof, may be implemented using other light-emitting technologies without departing from the principles of the invention; examples of other light-emitting technologies include, without limitation, organic LEDs, laser diodes, other semiconductor lasers.

Continuing with FIG. 1, the plurality of semiconductor devices 19 may be provided in the form of arrays 20, or an array of arrays (e.g., as shown in FIG. 1). The arrays 20 may be implemented so that one or more, or most of the semiconductor devices 19 are configured to provide radiant output. At the same time, however, one or more of the array's semiconductor devices 19 may be implemented so as to provide for monitoring selected of the array's characteristics. The monitoring devices 36 may be selected from among the devices in the array and, for example, may have the same structure as the other, emitting devices. For example, the difference between emitting and monitoring may be determined by the coupling electronics 22 associated with the particular semiconductor device (e.g., in a basic form, an LED array may have monitoring LED devices where the coupling electronics provides a reverse current, and emitting LED devices where the coupling electronics provides a forward current).

Furthermore, based on coupling electronics, selected of the semiconductor devices in the array may be either/both multifunction devices and/or multimode devices, where (a) multifunction devices may be capable of detecting more than one characteristic (e.g., either radiant output, temperature, magnetic fields, vibration, pressure, acceleration, and other mechanical forces or deformations) and may be switched among these detection functions in accordance with the application parameters or other determinative factors and (b) multimode devices may be capable of emission, detection and some other mode (e.g., off) and may be switched among modes in accordance with the application parameters or other determinative factors.

As described above, curing device 10 may be configured to receive a workpiece 26. As an example, workpiece 26 may be a UV-curable optical fiber, ribbon, or cable. Furthermore, workpiece 26 may be positioned at or near the foci of coupling optics 30 of curing device 10 respectively. In this manner, UV light irradiated from curing device 10 may be directed via coupling optics to the surface of the workpiece for UV curing and driving the photoreactions thereat. Further still, coupling optics 30 of curing device 10 may be configured to have a co-located focus, as will be further described below.

Turning now to FIG. 2, it illustrates an example spectrum 200 of a multi-wavelength (multi-λ) broad-band LED light source or curing device spanning the region of 300 nm<λ<580 nm LED curing lamp. As shown, the spectrum 200 comprises several dominant radiation emission peaks, including peaks 230, 236, 210, 240, 214, 216, and 218 substantially centered at wavelengths of 300 nm, 312 nm, 365 nm, 405 nm, 435 nm, 546 nm, and 575 nm, respectively.

As one example, the light source may comprise quantum-dot (QD) materials, for example a quantum dot layer, and a UV LED excitation source to create the dominant emission peak wavelengths shown in FIG. 2. Accordingly, the light source may be utilized in curing applications requiring lower energies (longer wavelengths) with the benefits, as compared to conventional gas discharge lamp technology, afforded by a solid-state (LED) curing lamp technology.

The UV LED excitation source capable of emitting the multi-λ emission spectrum 200 may comprise an LED array (e.g., and array of excitation LED's) emitting UV radiation at 365 nm, and a quantum dot layer comprising a combination or mixture of quantum dot materials having an absorption band based on a single excitation wavelength source, for example 365 nm. As such excitation LEDs of a single wavelength may provide the intrinsic excitation energy at the 365 nm peak to the quantum dot layer. For example, responsive to absorbing the 365 nm excitation wavelength radiation, the quantum dot layer may down-convert the absorbed first excitation wavelength radiation to lower-energy wavelengths at 435 nm, 546 nm, and 575 nm.

The quantum dot layer 50 may comprise a mixture or combination of quantum dot materials. The mixture of quantum dot materials may correspond to the number and value of the desired emission wavelengths. For example, the quantum dot layer 50 utilized for emitting the emission spectrum 200 may comprise three quantum dot materials, wherein the emission bands for each of the three quantum dot materials, in response to absorbing an excitation wavelength at 365 nm, comprise emission bands substantially centered at an emission wavelengths of 435 nm, 546 nm, and 575 nm, respectively. More specifically, one of the quantum dot materials may emit UV radiation substantially centered at 435 nm, a second quantum dot material may emit UV radiation substantially centered at 546 nm, and a third quantum dot material may emit UV radiation substantially centered at 575 nm, in response to absorbing UV radiation at 365 nm.

Herein, substantially centered may refer to a radiation at a wavelength value ±30 nm. For example, a peak 210 substantially centered at 365 nm, may include radiation emitted from 335 nm to 395 nm. As a further example, substantially centered may refer to a peak being centered at a wavelength number plus/minus 10 nm.

The quantum dot layer may also comprise a binding matrix or suspension material for supporting, fixing and/or maintaining the positions and distribution of the quantum dots in the quantum layer.

The spectral widths ($\Delta\lambda$) of the emitted radiation from the quantum dot layer 50 may be broader than those shown in the spectrum of FIG. 2, due to the broader emission spectrum from the excitation LEDs and the spectral widths of the emitted radiation from the quantum dot materials. To compensate for the broadening in spectral widths, the excitation and therefore the emission intensities at the various dominant wavelengths may be increased. Furthermore, the tuning of the excitation and emission spectrum intensity may depend on the curing application and may be tailored to the absorption characteristics of the workpiece to be cured.

Excitation radiation intensity may be adjusted by varying the intensity of the LED array, varying the number of LEDs in the array, and by using coupling optics such as micro-lenses and/or reflectors to, for example, collimate and/or focus the excitation radiation emitted from the LED array. Emission spectrum intensity and character (e.g. dominant wavelengths) of the quantum dot layer may be adjusted by varying the concentration of quantum dot materials within the quantum dot layer 50, by adjusting a thickness of the quantum dot layer, and by varying the type of quantum dot materials in the quantum dot layer. For example, the concentration of quantum dots of a first type, absorbing and down converting radiation of a first excitation wavelength and emitting radiation at a first excitation wavelength, may be adjusted by increasing or decreasing the concentration or number of quantum dots in the quantum dot layer 50. Accordingly, the relative intensities of the dominant emission wavelengths of the quantum dot layer emission spectrum can be adjusted by adjusting the relative quantities (e.g., concentration) of quantum dots of each type in the quantum dot layer 50. The proportions of the constituent quantum dot materials to be mixed together in the suspension material may be empirically determined. The differences in absorption and conversion efficiencies of each quantum dot material will drive the proportional mix of each quantum dot material based on an assumption of uniform excitation radiation emitted from each LED. Several iterations may be carried out to arrive at a desired spectral composition of the down-converted wavelengths at 435 nm 546 nm and 575 nm; relative to the 365 nm (first) excitation wavelength.

The amount of spectral energy at each of the dominant emission wavelengths of FIG. 2 may depend on the amplitudes and spectral widths characteristic of the absorption and emission curves of the quantum dot layer. Table 1 provides an example of quantification of relative emission energies from a quantum dot layer for approximating the emission spectrum of a mercury vapor arc lamp, for the given an excitation wavelength spectrum.

TABLE 1

| Mercury Arc Lamp | | | Quantum Dot (QD) layer |
|---|---|---|---|
| Wavelength (nm) | Relative Energy | Normalized Relative Energy (%) | QD Conversion Efficiency (%) |
| 300 | 13.3 | 14.7% | — |
| 312 | 36.4 | 17.9% | — |
| 365 | 55.6 | 18.9% | — |
| 405 | 22.4 | 8.4% | — |
| 435 | 59.7 | 12.6% | 60.0% |
| 545 | 47.5 | 10.5% | 80.0% |
| 576 | 57 | 16.8% | 80.0% |

Example quantum dot down-conversion efficiencies are listed in Table 1. These quantum dot efficiencies indicate that not all the excitation energy from the 365 nm excitation array of LED's may be down-converted to the lower energy wavelengths (e.g., 435 nm, 546 nm, 575 nm). The excitation light not down-converted to longer wavelengths may either be absorbed, resulting in non-radiative interactions adding to thermal loading (e.g., heat generation), or transmitted through the material at the incident 365 nm excitation wavelength. The relative percentages of absorption and transmission may depend on the characteristics of the quantum dot layer such as the concentration of quantum dots in the binding matrix, and the thickness of the quantum dot layer. In Table 1, example values for quantum dot down conversion efficiency are between 70%-80%.

Additional excitation LED's may be utilized to achieve the 300 nm, 312 nm, and 405 nm wavelengths of the spectrum 200. For example, the array 20 of light-emitting elements may comprise a plurality of arrays of LEDs, each array corresponding to an array of LED's emitting radiation at a first excitation wavelength, an array of LED's emitting radiation at a second excitation wavelength, and an array of LED's emitting radiation at a third excitation wavelength. For example, the first excitation wavelength may comprise 365 nm, the second excitation wavelength may comprise 300 nm, and the third excitation wavelength may comprise 405 nm. An additional array of LED's that emit radiation at an excitation wavelength of 312 nm may be provided. However, in some cases, the 312 nm LED's can be omitted from the photoreactive system, while still providing a reasonably close approximation of a Hg-arc lamp spectral envelope, provided sufficient energy contribution can be realized at the 300 nm wavelength.

As described above, the array 20 of light-emitting elements may thus include an array of arrays of LED's. As an example, the various arrays of LED's described above may be uniformly distributed in the array 20 of light-emitting elements to achieve uniform curing across a surface of a workpiece. As a further example, the various arrays of LED's may be non-uniformly distributed in the array 20 of light-emitting elements, in order to tailor a curing reaction corresponding to a custom workpiece, such as a workpiece with an irregular shape or surface or non-uniformly coated surface to be cured.

As such, the radiation emitted at the second and third excitation wavelengths onto the quantum dot layer may be transmitted, without absorption, and directed onto the workpiece to be cured. The radiation emitted at the first excitation wavelength may be only partially transmitted, and only partially absorbed and down converted, before being directed onto the workpiece to be cured. In this way, a multi-λ curing device comprising an array 20 of light-emitting elements and a quantum dot layer may be used to provide an emission spectrum approximating that of a mercury vapor arc lamp for curing a workpiece. Furthermore, an overall emission envelope of the multi-λ light source may comprise a convolution of the spectral bands from the array of LEDs comprising 365 nm LEDs, and the quantum dot emission spectra at 435 nm, 546 nm, and 575 nm, as well as the 300 nm LEDs, and 405 nm LEDs.

Turning now to FIGS. 3A and 3B, they illustrate an example of an LED array 300 for a curing device. FIG. 3A shows a plan view of LED array 300, comprising an array 320 of LED's mounted on a substrate 310. Substrate 310 may include a printed circuit board. As described above, array 320 of LED's may comprise first array of LED's 322 emitting light substantially centered at a first excitation wavelength, a second array of LED's 324 emitting light substantially centered at a second excitation wavelength, and a third array of LED's 328 emitting light substantially centered at a third excitation wavelength. As shown in FIG. 3A, the second array of LED's 324 and the third array of LED's 328 may be uniformly dispersed within the first array of LED's 322. In one example, the first excitation wavelength comprises 365 nm, the second excitation wavelength comprises 300 nm, and the third excitation wavelength comprises 405 nm. Furthermore, the array 320 of LED's comprises a plurality of sub-arrays 316 of LED's, each including LED's 322, 324, and 328. The array 320 of LED's may be organized into a plurality of sub-arrays for mitigating heat generation, or to enable independent control of individual sub-arrays 316 of LED's, as examples.

FIG. 3B shows a cross-sectional view of the LED array 320 of FIG. 3A taken at section 3B-3B. The LED array 320 may further comprise a micro-lens array 350, wherein each micro-lens in the micro-lens array 350 may correspond to an LED of LED array 320. The micro-lens array may be index-matched to the LED's and may aid in collimating, focusing, dispersing, and the like the emitted radiation from the LED's. Furthermore, the micro-lens array may be positioned directly adjacent to and in face-sharing contact with the LED array 320.

Turning now to FIGS. 4A and 4B, they illustrate an example of an LED array 400 for a curing device. FIG. 4A shows a plan view of LED array 400, comprising an array 420 of LED's mounted on a substrate 310. Array 420 may comprise a first array of LED's 322 emitting light at a first excitation wavelength, a second array of LED's 324 emitting light at a second excitation wavelength, and a third array of LED's 328 emitting light at a third excitation wavelength. In one example, the first excitation wavelength comprises 365 nm, the second excitation wavelength comprises 300 nm, and the third excitation wavelength comprises 405 nm.

As shown in FIG. 4B, array 420 of LED's may further comprise micro-lens array 320. In one example, array 420 of LED's may also comprise a quantum dot layer 450 positioned directly adjacent to and in face-sharing contact with the micro-lens array 350. In some cases, array 420 may not include micro-lens array 350 and quantum dot layer 450 may be positioned directly adjacent to and in face-sharing contact with the array of light-emitting elements (e.g., LED array 420). As such, the quantum dot layer 450 may be applied in a direct-to-emitter manner.

Furthermore, the quantum dot binding matrix may include a suspension mixture positioned or applied directly to either some or all of the 365 nm excitation LEDs. The fraction of LEDs to be coated with the quantum dot layer may depend on the thickness and concentration of the quantum dot layer 450 and the absorbing/down conversion and transmitting character of the quantum dot layer 450 relative to the excitation wavelength radiation. For example, the thickness of the quantum dot layer 450 and concentration of the quantum dots in the quantum dot layer 450 may determine the relative amount of excitation light that transmits through the quantum dot layer 450 without being absorbed by the quantum dot material mixture. In some examples, all the excitation LEDs provided in array 420 of LED's may be coated with the quantum dot layer. For example, all the LED's of array 420 may be coated with the quantum dot layer 450 in cases where the quantum dot layer is thin enough, and/or the quantum dot concentration is low enough, to allow enough of the first excitation wavelength radiation to be transmitted to the workpiece at an amplitude sufficient to meet the desired spectral content.

The application of the quantum dot material directly to the LED's or light-emitting elements enables an increase in the emitted irradiance and the down-conversion efficiency from the quantum dot material mixture, as compared to the case when the quantum dot material is not applied directly to the LED's.

The number of LED's used for quantum dot conversion may depend on the relative numbers of the constituent quantum dot material types, the desired power and/or irradiance needed from the array, and the relative amount of excitation light needed at a an excitation wavelength. For example, if the concentration of quantum dots for down converting an excitation wavelength is higher, then the number of LED's or the intensity of LED's emitting radiation at said excitation wavelength may be reduced. Accordingly, the number of LED's of each type (e.g., each type emitting radiation of a different excitation wavelength), the intensity of LED's of each type, and the concentration of quantum dot material types may be correspondingly adjusted to achieve the desired emission spectrum for curing a workpiece.

Furthermore, other LEDs (e.g. 300 nm, 312 nm, 405 nm, whose excitation wavelengths are not absorbed and down converted by the quantum dot layer may be used in the array for generating higher-energy (shorter wavelength) radiation at the workpiece to approximate the spectrum of a conventional Hg-arc lamp. The relative density (number) of these non-down converting LED emitters used may depend on the curing power needed at the shorter wavelengths, as compared to the amount of power being generated by the LED's whose excitation wavelength radiation is down-converted by the quantum dot layer. The relative density of these non-down converting LED's may be determined empirically for a given array and size, and curing application. Table 1 may provide a guide as to the relative percentages of energy needed at the various constituent wavelengths for approximating the spectrum of a conventional mercury vapor arc lamp.

The quantum dot layer 450 may be directly applied to the LED's in a similar manner to the way in which a micro-lens array material is applied. For example, a polymeric suspension (e.g., quantum dot layer binding matrix) may be applied over the LED's, and then molded and cured, the quantum dot layer being allowed to dry forming a permanent layer over the excitation LED's. As described above and shown in FIGS. 3A-3B and 4A-4B, the LED array may be configured with or without micro-lenses, although increased light extraction (and hence maximum down-conversion efficiency of the quantum dot layer) may be achieved with the micro-lenses applied.

Turning now to FIG. 5, it illustrates a perspective view of an example curing device 500. Curing device 500 may comprise a protective housing 560, including a front cover plate 514, and fasteners 512 such as screws or clips. Front cover plate 514 may include a transparent opening and/or window 530 through which UV radiation is emitted via an array of LED's 520. Window 530 may be rectangular as shown, but may also comprise other geometries. The size and shape of window 530 may depend on the curing application and the area over which a workpiece surface is to be cured. The array of LED's 520 may comprise a micro-lens array for collimating/focusing/dispersing light emitted from the LED's, and may also comprise a quantum dot layer applied over the LED's as described above. The array of LED's 520 may be mounted on a substrate such as a printed circuit board, and conductive heat sinks 540 may be mounted to the substrate proximally to the LED's for dissipating heat during operation of curing device 500. Protective housing 560 may contain wiring and other electronic components of the lighting subsystem, as well as a power source, controller, cooling subsystem, and components thereof.

Figure 6A:
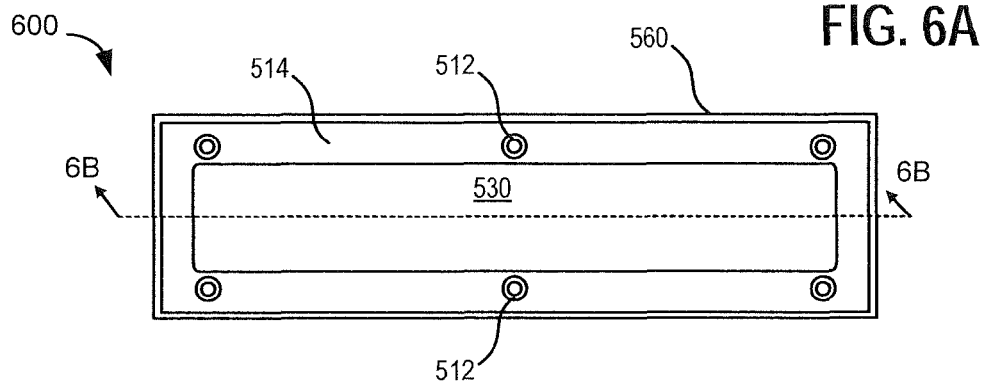
FIG. 6A illustrates a front view of an example curing device.

Turning now to FIG. 6A, it illustrates a front view schematic of UV curing device 600, including window 530, protective housing 560, front cover plate 514, and fasteners 512. As shown in FIG. 6A, the size and shape of the UV curing device 600 and protective housing 560 may be flat and oblong, depending on the curing application, as compared to the UV curing device 500 shown in FIG. 5. Furthermore, window 530 may be more elongated and may be slightly smaller than front cover plate 514. For example, the flatter, elongated shape of UV curing device 600 combined with the size of window 530 being slightly smaller than front cover plate 514, may facilitate stacking of multiple UV curing devices while maintaining curing uniformity.

Figure 6B:
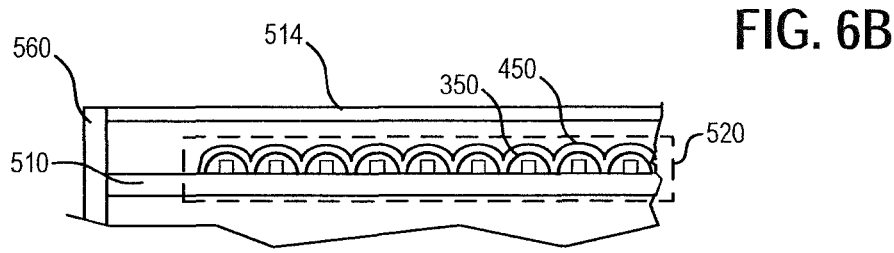
FIG. 6B illustrates a cross-section of example curing device of FIG. 6A.

Turning now to FIG. 6B, it illustrates a cross section of the UV curing device 600 taken at 6B-6B. As shown, UV curing device 6B comprises a quantum dot layer 450 applied directly to the array of LED's 520 in a direct-to-emitter configuration. Furthermore, window 530 may be index-matched to the array of LED's 520 to reduce the amount of incident light from the curing device that is reflected or dispersed at the window 530.

Figure 7A:
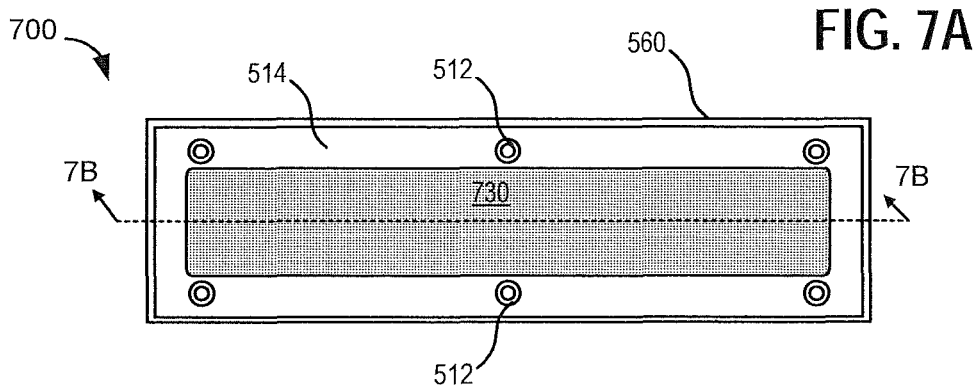
FIG. 7A illustrates a front view of an example curing device.
Figure 7B:
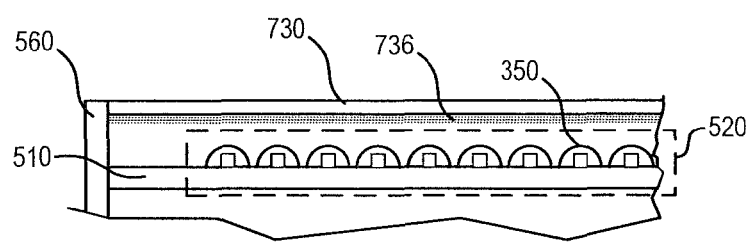
FIG. 7B illustrates a cross-section of example curing device of FIG. 7A.

Turning now to FIG. 7A, it illustrates a curing device 700 comprising a quantum dot layer having a direct-to-window configuration. In the direct-to-window configuration of curing device 700, window 730 includes a quantum dot layer 736 is positioned directly adjacent to and in face-sharing contact with a surface of window 730. FIG. 7B illustrates a cross-sectional view of UV curing device 700 taken at section 7B-7B. Quantum dot layer 736 is positioned directly adjacent to and in face-sharing contact with the surface of window 730 facing the array of LED's 520. In the direct-to-window configuration, a quantum dot layer may not be positioned directly adjacent to the array of LED's 520 or to a micro-lens array 350 directly adjacent to and in face-sharing contact with the array of LED's 520. Furthermore, the proximity of the window 730 to the array of LED's 520 may vary depending on the irradiance and curing device output specifications. For example, the window 730 may be positioned farther from the array of LED's 520 in order to reduce the output intensity of the curing device as compared to when the window 730 is positioned closer to the array of LED's 520.

In the direct-to-window configuration, a quantum dot layer suspension, comprising a quantum dot mixture and a binding matrix is applied to the inside surface of window 730. Application of the quantum dot layer may comprise a silk screen, doctor blade, or squeegee type application method, as known in the art. For example, the quantum dot materials may be mixed in a carrier suspension, for example an epoxy or polymeric resin, which is then applied in a relatively thin layer to the surface of the window 730. As described above for the direct-to-emitter configuration, the thickness of the applied quantum dot layer will depend on the quantum dot conversion efficiency, the amount of excitation irradiance from the array of LED's 520, and the amount of unabsorbed excitation irradiance needed to transmit through the film for efficient curing of the workpiece. In general, when the first excitation wavelength comprises radiation substantially centered at 365 nm, not all of the excitation light at 365 nm will be absorbed. Some radiation will be transmitted through the quantum dot layer without substantial absorption, the fraction of which will depend on the concentration and thickness of the applied quantum dot layer. As with the Direct-to-Emitter approach, the optimized layer thickness of the applied quantum dot material may be determined empirically for a particular application. For example, thinner quantum dot layers may transmit a greater portion of the first excitation wavelength radiation as compared to thicker quantum dot layers (given the same concentration of quantum dot materials) due to the lower number of quantum dots encountered by the radiation emitted onto and passing through the quantum dot layer.

In some examples, the quantum dot layer may be applied to the window in a patterned manner, for example in a fine mesh or screened pattern. Patterning the quantum dot layer onto the window may be another way to control the transmission and absorption characteristics of the quantum dot layer. In particular, regions of the patterned quantum dot layer which are thinner or have a lower concentration of quantum dot material may transmit a greater fraction of excitation wavelength radiation, as compared to regions which are thicker or have a higher concentration of quantum dot material. Patterning the quantum dot layer may also be used to control the rate of curing across a workpiece surface in a non-uniform manner. As a simple example, a striped quantum dot layer comprising thicker parallel strips of quantum dot material separated by parallel strips of thinner quantum dot material may be employed.

The direct-to-window configuration lends itself to various established deposition techniques used in manufacturing where thin viscous material is applied to a flat surface; (e.g. adhesive for surface bonding). In addition, it may be simpler to retrofit existing curing devices and/or LED array light sources using the direct-to-window configuration, for example, by replacing an existing window with a quantum dot layer-coated window. For these reasons, the direct-to-window approach may be a simpler and more attractive configuration as compared to the direct-to-emitter configuration. However, as described above, the direct-to-emitter configuration may achieve higher irradiance and higher down-conversion efficiencies of the absorbed excitation wavelength radiation.

In this manner, a curing device may comprise a first array of LED's, each LED of the first array emitting radiation substantially centered at a first excitation wavelength onto a quantum dot layer, the quantum dot layer positioned above the first array of LED's and configured to partially absorb the first excitation wavelength radiation and down convert the absorbed first excitation wavelength radiation, and partially transmit the emitted first excitation wavelength radiation, wherein the down converted and the partially transmitted first excitation wavelength radiation are directed onto a radiation-curable workpiece.

The curing device may further comprise a second array of LED's, each LED of the second array emitting radiation substantially centered at a second excitation wavelength onto the quantum dot layer, wherein the quantum dot layer is configured to transmit the emitted second excitation wavelength radiation onto a radiation-curable workpiece.

The curing device may further comprise a window positioned above the first array of LED's, wherein the quantum dot layer is positioned directly adjacent to a surface of the window facing the first array of LED's. The quantum dot layer may be positioned above and in face-sharing contact with the first array of LED's. Furthermore, the curing device may comprise an array of micro-lenses positioned directly over and in face-sharing contact with the array of LED's, each micro-lens corresponding to an LED in the first array of LED's, wherein the quantum dot layer is positioned directly over and in face-sharing contact with the array of micro-lenses.

The first excitation wavelength may comprise 365 nm, the down converted radiation may comprise radiation at one or more of 435 nm, 545 nm, and 575 nm, and the second excitation wavelength may comprise one of 300 nm, and 405 nm.

Turning now to FIG. 8, it illustrates an example method 800 of curing a workpiece. In one example, method 800 may be executed by a controller of a photoreactive system such as a UV curing device for curing a workpiece. Method 800 begins at 810 where first excitation wavelength radiation is emitted onto a quantum dot layer. As described above, the first excitation wavelength radiation may comprise UV radiation substantially centered at 365 nm. The first excitation wavelength radiation may be emitted from an array of LED's, and the first excitation wavelength radiation may be focused, collimated, dispersed, and the like from a micro-lens array prior to being emitted onto the quantum dot layer. In some examples, the controller may adjust the power input to the LED array (or part of the LED array) to control the irradiance (intensity) of the emitted radiation.

The quantum dot layer may comprise a mixture of quantum dot materials suspended in a matrix such that the first excitation wavelength radiation is partially absorbed by the quantum dot layer and down converted into one or more longer wavelength radiation components. For example, the quantum dot layer may comprise three types of quantum dot materials so that the 365 nm excitation radiation may be only partially absorbed by the quantum dot layer and down converted to 435 nm, 545 nm, and 575 nm components. Each down converted component may correspond to one of the quantum dot material types. For instance the first, second, and third quantum dot material types may down convert the 365 nm excitation radiation to 435 nm, 545 nm, and 575 nm, respectively. The intensity of each of the down converted components may be proportional to the concentration of each type of quantum dot material in the quantum dot layer. For example, increasing the concentration of the first quantum dot material type may increase the intensity of the corresponding down converted radiation component. In this way, the concentrations of the quantum dot materials in the quantum dot layer may be tailored to design a quantum dot layer tuned to a particular curing application.

The first excitation wavelength radiation may also be only partially transmitted through the quantum dot layer, without substantial absorption and without substantial down conversion. In other words, the portion of the first excitation wavelength radiation that is not absorbed and down converted by the quantum dot layer is instead transmitted through the quantum dot layer. Furthermore, UV radiation emitted onto the quantum dot layer that is not substantially centered at 365 nm may be transmitted without substantial absorption and without substantial down conversion onto the workpiece.

Accordingly method 800 continues at 820 where the first excitation wavelength radiation is only partially transmitted through the quantum dot layer onto the radiation-curable workpiece, and at 830 and 840, where the first excitation wavelength radiation is only partially absorbed and then down converted at the quantum dot layer, respectively. Next at 850, method 800 directs the down converted first excitation wavelength radiation onto the radiation-curable workpiece. As an example, the curing device may be positioned opposite a radiation-curable workpiece, such that radiation is emitted from the curing device directly onto the workpiece.

Next, at 860 and 870, method 800 determines if second and third excitation wavelength radiation, respectively is to be emitted onto the quantum dot layer. At 866 and 876, the second and third excitation wavelength radiation is transmitted through the quantum dot layer (without substantial absorption or substantial down conversion) onto the radiation-curable workpiece. As described above, the LED array of the UV curing device may comprise arrays of LED arrays. Each individual array of LED's may comprise a different type of LED, wherein each type of LED may emit a different wavelength of radiation. For example, an array of LED's may emit radiation of a second excitation wavelength such as 300 nm. The 300 nm wavelength radiation may not be absorbed or down converted by the quantum dot layer, and instead be transmitted directly through the quantum dot layer onto the radiation-curable workpiece. Accordingly, by selecting arrays of LED's to emit a second excitation wavelength of 300 nm and 405 nm, respectively, a spectrum of radiation emitted by the UV curing device may more closely approximate or mimic the spectrum emitted by a conventional mercury vapor arc lamp. Furthermore, by choosing to include various arrays of LED's in the UV curing device, various emission spectra can be provided and thus tailored to a specific curing application. Further still, the excitation emission spectrum may comprise a combination of excitation radiation wavelengths, wherein excitation radiation at a first excitation wavelength is only partially absorbed and down converted at the quantum dot layer, and excitation radiation at a second or third excitation wavelength is transmitted through the quantum dot layer without substantial absorption and without substantial down conversion at the quantum dot layer onto the radiation-curable workpiece.

In this manner, a method of curing a workpiece may comprise emitting radiation substantially centered at a first excitation wavelength from an array of LED's onto a quantum dot layer, only partially transmitting the first excitation wavelength radiation through the quantum dot layer onto a radiation-curable workpiece, only partially absorbing the emitted first excitation wavelength radiation at the quantum dot layer, and responsive to absorbing the excitation wavelength radiation, down converting the absorbed first excitation wavelength radiation at the quantum dot layer and emitting the down converted radiation onto the radiation-curable workpiece. The method may further comprise emitting radiation substantially centered at a second excitation wavelength from the array of LED's onto the quantum dot layer, wherein the second excitation wavelength radiation is transmitted to the workpiece without substantial absorption at the quantum dot layer. Furthermore, the method may comprise emitting radiation substantially centered at a third excitation wavelength from the array of LED's onto the quantum dot layer, wherein the third excitation wavelength radiation is transmitted to the workpiece without substantial absorption at the quantum dot layer. The first excitation wavelength radiation substantially centered at 365 nm may be emitted from the array of LED's, the second excitation wavelength radiation substantially centered at 300 nm may be emitted from the array of LED's, and the third excitation wavelength radiation substantially centered at 405 nm may be emitted from the array of LED's.

Furthermore, the method may comprise collimating the first excitation wavelength radiation at an array of micro-lenses in face-sharing contact with the array of LED's, prior to only partially absorbing and down converting the first excitation wavelength radiation at the quantum dot layer.

In this manner, a method may comprise emitting UV radiation onto a quantum dot layer, only partially absorbing and down converting the UV radiation substantially centered at 365 nm at the quantum dot layer, and only partially transmitting the UV radiation substantially centered at 365 nm through the quantum dot layer. The method may further comprise transmitting, without substantial absorption, the UV radiation substantially centered at 300 nm and the UV radiation substantially centered at 405 nm through the quantum dot layer. The UV radiation substantially centered at 365 nm may be down converted to one or more of UV radiation substantially centered at 435 nm, 546 nm, and 575 nm.

Furthermore, the method may comprise directing the down converted UV radiation substantially centered at 365 nm onto a UV-curable workpiece, directing the partially transmitted UV radiation substantially centered at 365 nm onto a UV-curable workpiece, and directing the transmitted UV radiation not substantially centered at 365 nm onto a UV-curable workpiece. Further still, the method may comprise transmitting, without substantial absorption, the UV radiation not substantially centered at 365 nm through the quantum dot layer.

It will be appreciated that the configurations disclosed herein are exemplary in nature, and that these specific embodiments are not to be considered in a limiting sense, because numerous variations are possible. For example, the above embodiments can be applied to various types of workpieces. Furthermore, the UV curing devices and systems described above may be integrated with existing manufacturing equipment and are not designed for a specific light source. As described above, any suitable light engine may be used such as a microwave-powered lamp, LED's, LED arrays, and mercury arc lamps. The subject matter of the present disclosure includes all novel and non-obvious combinations and subcombinations of the various configurations, and other features, functions, and/or properties disclosed herein.

Note that the example process flows described herein can be used with various UV curing devices and UV curing system configurations. The process flows described herein may represent one or more of any number of processing strategies such as continuous, batch, semi-batch, and semi-continuous processing, and the like. As such, various acts, operations, or functions illustrated may be performed in the sequence illustrated, in parallel, or in some cases omitted. Likewise, the order of processing is not necessarily called for to achieve the features and advantages of the example embodiments described herein, but is provided for ease of illustration and description. One or more of the illustrated acts or functions may be repeatedly performed depending on the particular strategy being used. It will be appreciated that the configurations and routines disclosed herein are exemplary in nature, and that these specific embodiments are not to be considered in a limiting sense, because numerous variations are possible. The subject matter of the present disclosure includes all novel and non-obvious combinations and subcombinations of the various systems and configurations, and other features, functions, and/or properties disclosed herein.

The following claims particularly point out certain combinations and subcombinations regarded as novel and non-obvious. These claims may refer to "an" element or "a first" element or the equivalent thereof. Such claims are to be understood to include incorporation of one or more such elements, neither requiring nor excluding two or more such elements. Other combinations and subcombinations of the disclosed features, functions, elements, and/or properties may be claimed through amendment of the present claims or through presentation of new claims in this or a related application. Such claims, whether broader, narrower, equal, or different in scope to the original claims, also are regarded as included within the subject matter of the present disclosure.

The invention claimed is:

1. A curing device, comprising:
a first array of LEDs with a micro-lens array, each LED of the first array emitting radiation that is focused by the micro-lens array and substantially centered at a first excitation wavelength onto a quantum dot layer, the quantum dot layer positioned above the first array of LEDs and configured to
partially absorb the first excitation wavelength radiation and down convert the absorbed first excitation wavelength radiation, and
partially transmit the emitted first excitation wavelength radiation,
wherein the down converted and the partially transmitted first excitation wavelength radiation are directed onto a radiation-curable workpiece, and
wherein each micro-lens is positioned directly over and in face-sharing contact with a corresponding LED in the first array of LEDs, wherein the quantum dot layer is positioned directly over and in face-sharing contact with the array of micro-lenses.

2. The curing device of claim 1, further comprising a second array of LEDs, each LED of the second array emitting radiation substantially centered at a second excitation wavelength onto the quantum dot layer, wherein the quantum dot layer is configured to transmit the emitted second excitation wavelength radiation onto the radiation-curable workpiece.

3. The curing device of claim 2, wherein the second excitation wavelength comprises one of 300 nm and 405 nm.

4. The curing device of claim 1, further comprising a window positioned above the first array of LEDs, wherein the quantum dot layer is positioned directly adjacent to a surface of the window facing the first array of LEDs.

5. The curing device of claim 1, wherein the quantum dot layer is positioned above and in face-sharing contact with the first array of LEDs.

6. The curing device of claim 1, wherein the first excitation wavelength comprises 365 nm and is partially transmitted to effectuate curing of the radiation-curable workpiece.

7. The curing device of claim 1, wherein the down converted radiation comprises radiation at one or more of 435 nm, 545 nm, and 575 nm.

8. A method of curing a workpiece, comprising:
emitting radiation substantially focused and substantially centered at a first excitation wavelength from an array of LEDs onto a quantum dot layer;
only partially transmitting the first excitation wavelength radiation through the quantum dot layer onto a radiation-curable workpiece;
only partially absorbing the emitted first excitation wavelength radiation at the quantum dot layer;
responsive to absorbing the first excitation wavelength radiation, down converting the absorbed first excitation wavelength radiation at the quantum dot layer and emitting the down converted radiation onto the radiation-curable workpiece; and
collimating the first excitation wavelength radiation at an array of micro-lenses in face-sharing contact with the array of LEDs, prior to only partially absorbing and down converting the first excitation wavelength radiation at the quantum dot layer.

9. The method of claim 8, further comprising emitting radiation substantially centered at a second excitation wavelength from the array of LEDs onto the quantum dot layer, wherein the second excitation wavelength radiation is transmitted to the workpiece without substantial absorption at the quantum dot layer.

10. The method of claim 9, further comprising emitting radiation substantially centered at a third excitation wavelength from the array of LEDs onto the quantum dot layer, wherein the third excitation wavelength radiation is transmitted to the workpiece without substantial absorption at the quantum dot layer.

11. The method of claim 10, wherein the second excitation wavelength radiation substantially centered at 300 nm is emitted from the array of LEDs, the method further comprising curing the radiation-curable workpiece with the transmitted and emitted radiation.

12. The method of claim 11, wherein the third excitation wavelength radiation substantially centered at 405 nm is emitted from the array of LEDs, the method further comprising curing the radiation-curable workpiece with the transmitted and emitted radiation.

13. The method of claim 8, wherein the first excitation wavelength radiation substantially centered at 365 nm is emitted from the array of LEDs, the method further comprising curing the radiation-curable workpiece with the transmitted and emitted radiation.

\* \* \* \* \*